United States Patent
Veneroni et al.

(10) Patent No.: US 9,498,615 B2
(45) Date of Patent: Nov. 22, 2016

(54) INSERT FOR THE INFUSION OF DRUGS

(75) Inventors: Alain Veneroni, Spino d'Adda (IT); Massimo Fini, Mirandola (IT)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1179 days.

(21) Appl. No.: 13/519,711

(22) PCT Filed: Jan. 17, 2011

(86) PCT No.: PCT/EP2011/050517
§ 371 (c)(1),
(2), (4) Date: Jun. 28, 2012

(87) PCT Pub. No.: WO2011/092068
PCT Pub. Date: Aug. 4, 2011

(65) Prior Publication Data
US 2012/0302967 A1    Nov. 29, 2012

(30) Foreign Application Priority Data

Jan. 29, 2010  (EP) ..................................... 10152140

(51) Int. Cl.
*A61M 39/26* (2006.01)
*A61M 5/162* (2006.01)

(52) U.S. Cl.
CPC .............. *A61M 39/26* (2013.01); *A61M 5/162* (2013.01); *A61M 2039/267* (2013.01); *A61M 2039/268* (2013.01)

(58) Field of Classification Search
CPC ............... A61M 5/162; A61M 39/26; A61M 2039/267; A61M 2039/268
See application file for complete search history.

(56) References Cited

U.S. PATENT DOCUMENTS

| 4,270,725 | A |   | 6/1981  | Scott et al. |
|-----------|---|---|---------|--------------|
| 4,410,321 | A | * | 10/1983 | Pearson ................ A61J 1/2089 604/410 |
| 4,759,756 | A |   | 7/1988  | Forman et al. |
| 4,936,841 | A | * | 6/1990  | Aoki ..................... A61J 1/2089 206/222 |
| 5,086,813 | A | * | 2/1992  | Galloway ............... B67D 7/02 141/1 |
| 6,022,339 | A |   | 2/2000  | Fowles et al. |

FOREIGN PATENT DOCUMENTS

| EP | 0 172 836    | 8/1985  |
| EP | 0 713 409    | 12/2001 |
| EP | 1 731 185    | 12/2006 |
| EP | 09 175 001.8 | 5/2011  |
| JP | 2006-015024  | 1/2006  |
| WO | WO 2004/108058 | 12/2004 |

* cited by examiner

*Primary Examiner* — Kevin C Sirmons
*Assistant Examiner* — Shefali Patel
(74) *Attorney, Agent, or Firm* — Jacobson Holman, PLLC.

(57) ABSTRACT

An insert for an infusion of drugs is configured for connection to a vial and preferably to a circuit or an infusion line. The insert includes a main body, a resilient element, and a piercing spike. The piercing spike has an axis X and defines a first channel and a second channel, and is movable relative to the main body along the axis X between a first closed position A and a second open position B. The resilient element presses against the piercing spike so as to keep the piercing spike in the first closed position A when no external forces are applied.

18 Claims, 5 Drawing Sheets

INSERT FOR THE INFUSION OF DRUGS

CROSS-REFERENCE TO RELATED APPLICATIONS

This is a national stage of PCT/EP11/050517 filed Jan. 17, 2011 and published in English, which claims the priority of European number 10152140.9 filed Jan. 29, 2010, hereby incorporated by reference.

BACKGROUND OF THE INVENTION

1. Field of Invention

The invention relates to an insert for the transfer of liquids from vials, for example for the infusion of drugs in a circuit or an infusion line. With regard to the invention a circuit is preferably an extracorporeal circuit and most preferably a hemodialysis circuit. In particular the invention relates to an insert suitable for receiving, engaged thereon, a drug-containing vial.

2. Description of the Prior Art

There are several circumstances in which transfer of a liquid is required from a vial to another circuit. Such circumstances may occur, for example, during therapeutic treatments like intravenous therapy or when a liquid needs to be transferred from a vial to another container. In the following description, specific reference is made to another very important field where liquids need to be transferred from a vial to a circuit, i.e. the field of therapeutic treatments carried out by means of an extra-corporeal circuit, in particular a hemodialysis circuit. Such reference has no limiting intent, since the invention can be effectively used in other fields.

During therapeutic treatment which requires an extra-corporeal circulation it is often required to administer various drugs to the patient. The presence of the extra-corporeal circuit advantageously avoids the need to administer the drug by means of an injection performed directly on the patient.

By way of example haemodialysis treatment is considered below, without the scope of the invention being limited to this specific application.

During haemodialysis it is often required to administer various drugs or therapeutic substances, such as iron, heparin, erythropoietin and vitamins. The infusion of such substances into the extra-corporeal circuit is at present performed by means of conventional syringes. The substance is drawn from the vial in which it is supplied by the manufacturer and is then injected into a special insert provided along the circuit and equipped with a piercible cap. A double transfer of the substance is therefore performed: first from the vial into the syringe and then from the syringe into the circuit.

This operation thus requires the use of disposable materials, such as the syringe in the respective needle, merely in order to transfer the substance from the vial into the circuit. Moreover, the use of needles always involves the risk of the operating staff being pricked.

Moreover, some of the substances mentioned must be administered slowly over a period of a few minutes. It can therefore be easily understood how the administration of various substances to more than one patient represents a considerable amount of work for the nursing staff responsible for the haemodialysis treatment.

Assemblies for the infusion of substances in an extracorporeal circuit are described for example in detail in the documents EP 0 172 836 and EP 0 713 409. The object of the present invention is therefore to solve at least partially the problems mentioned in connection with the infusion inserts of the known type.

SUMMARY OF THE INVENTION

One task of the present invention is to provide an insert which allows direct engagement of the vial in which the drug is supplied and therefore avoids a double transfer of the substance.

Another task of the present invention is to provide an insert which avoids the use of conventional syringes and the associated needles.

Another task of the present intention is to provide an insert which opens the circuit only when a vial is connected to it and which, on the other hand, closes the circuit again upon removal of the vial.

Another task of the present invention is to provide an insert which allows the slow administration of the substances without requiring for this purpose the active presence of the operating staff.

Another task of the present invention is to provide an insert which is adapted to avoid contamination and to enhance sterility of the overall circuit.

The abovementioned object and tasks are achieved by an infusion insert as described herein.

BRIEF DESCRIPTION OF THE DRAWINGS

The characteristic features and further advantages of the invention will emerge from the description provided hereinbelow, of a number of examples of embodiment, provided purely by way of a non-limiting example, with reference to the accompanying drawings in which:

FIG. 3.a shows schematically the detail of an insert for infusing substances according to the invention and a vial known per se;

FIG. 3.b shows schematically the detail of another insert for the infusion of substances according to the invention;

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention relates to an insert 20 for the infusion of drugs. The insert 20 is suitable for connection to a vial 18 and preferably to an extracorporeal circuit 16 or an infusion line. Moreover the insert 20 comprises a main body 22, a resilient element 24 and a piercing spike 26.

The piercing spike 26 has an axis X and defines a first channel 261 and a second channel 262 and is movable relative to the main body 22 along the axis X between a first closed position A and a second open position B. Moreover the resilient element 24 acts on the piercing spike 26 so as to keep it in the first closed position A when no external forces are applied.

In the description of the invention, reference will be made to the spatial arrangement of the insert 20 which allows correct operation thereof. During operation of the insert 20, in fact, the force of gravity plays a decisive part, especially in certain embodiments. In particular, it will be assumed below that the force of gravity is directed as shown by the vector g in FIGS. 3 to 9. The vector g therefore defines the vertical direction and is oriented from the top downwards. In view of the above, the expressions "top", "upper" and the like will be used below to indicate positions which are relatively distant from the ground and, on the other hand, the expressions "bottom", "lower" and the like will be used to indicate positions relatively close to the ground.

Preferably, a standard vial 18 is considered below, i.e. a vial 18 which has a cylindrical head 180 with a predefined diameter d and height h (see FIG. 3). On the other hand, the body 181 of the vial may be of any shape or size. For example, a vial 18 is preferably considered below in accordance to standard DIN/ISO 8362-1, more preferably of the 2R or 4R type.

A non-standard vial 18 (not shown) can also be used in connection with the insert 20 according to the invention. In this regard it should be noted that the seat 227 defined by the main body 22 (disclosed in detail below) must match with the head 180 of the non-standard vial 18. In other words, non-standard vials 18 may be used in connection with inserts 20 in which the seat 227 is specifically designed, with respect to its size and shape, for matching a specific type of non-standard head 180 of a vial 18. Preferably the diameter d of the vial head 180 is 13 mm.

The piercing spike 26 is rigid and pointed at its top end. In this way it is suitable for perforating easily the stopper 182 which is usually arranged on a standard vial containing substances for therapeutic use. The piercing spike 26 extends mainly along the axis X, but it preferably also comprises a flange 263 which extends in a plane perpendicular to X. In accordance with the embodiment shown in the accompanying figures, radial lugs 265 extend from the flange 263.

The first channel 261 and the second channel 262 extend along the piercing spike 26 preferably parallel to each other and to the axis X. In accordance with the embodiment shown in the accompanying figures, the channels 261 and 262 start at the top of the spike 26, extend axially over most of its length and, at the bottom of the spike 26, terminate with a radial progression. Just further below the end of the channels 261 and 262 the spike 26 may comprise bulges 267. The spike 26 extends below and beyond the end of the channels 261 and 262 and beyond the bulges 267 so as to define an end-piece or tang 264.

In accordance with one embodiment, the spike 26 is made of a rigid material, preferably is made of a rigid polymer. Polymers which are suitable for such use are for example: polycarbonate (PC), polypropylene (PP), polyethylene (PE), polystyrene (PS), polyvinyl chloride (PVC), polyethylene terephthalate (PET), polybutylene terephthalate (PBT), acrylonitrile-butadiene-styrene (ABS), and copolyesters.

In accordance with the embodiment shown in the accompanying figures, the resilient element 24 receives the bottom part of the spike 26, defining a seat 246 inside which the spike 26 is seated with slight interference. The spike 26 may slide inside the seat 246, passing from the closed position A into the open position B and/or vice versa.

In accordance with the embodiment shown in the accompanying figures, the resilient element 24 also defines a resilient thrusting surface 244 able to push the spike 26 in the axial direction, in particular towards the closed position A. In other words, the resilient thrusting surface 244 presses against the tang 264 with an upwardly directed force.

In accordance with the embodiment shown in the accompanying figures, the resilient element 24 also defines internally a first channel 241 and a second channel 242. The channels 241 and 242 connect the seat 246 to the outside of the insert 20 and are intended to define respective extensions of the first channel 261 and the second channel 262 defined by the spike 26. The resilient element 24 may also define cavities 247 suitable for seating the bulges 267 of the spike 26.

In accordance with one embodiment, the resilient element 24 is made of an elastic material, preferably an elastomer. Elastomers which are suitable for such use are for example: Silicone Rubber, Styrene-Ethylene-Butylene-Styrene (SEBS), Styrene-Ethylene-Propylene-Styrene (SEPS), Styrene-Isoprene-Styrene (SIS), Styrene-Butadiene-Styrene (SBS), Poly-Urethane (PU), Natural Rubber (NR) and latex.

In accordance with the embodiment shown in the accompanying figures, the main body 22 defines a seat for the resilient element 24, for the spike 26 and for the head 180 of the vial 18. The main body 22 comprises upper rests 223 for defining a top end-of-travel stop for the spike 26, while the bottom end-of-travel stop for the spike 26 is defined by the contact on the resilient element 24. In particular, the top stop defines the closed position A, while the bottom stop defines the open position B.

The main body 22 defines a seat for the resilient element 24 and comprises a first channel 221 and a second channel 222 suitable for extending, respectively, the first channel 241 and the second channel 242 of the resilient element 24.

As mentioned above, the main body 22 also defines a seat 227 suitable for seating the head 180 of the vial 18. In particular, in the embodiment shown, the seat 227 comprises teeth 228 for providing a snap-engaging connection between the main body 22 of the insert 20 and the head 180 of the vial 18.

In accordance with one embodiment, the main body 22 is made of a rigid material, preferably of a rigid polymer. Polymers which are suitable for such use are for example those listed above with respect to spike 26.

In accordance with one embodiment of the invention, the main body 22 and the resilient element 24 are manufactured by means of two-component injection moulding. According to two-component injection moulding, in a manner known per se, the first melt (intended to originate the rigid polymer after polymerization) and the second melt (intended to originate the elastomer after polymerization) are fed, one after the other or simultaneously, into one single mould.

With reference to the accompanying figures, the operating principle of the insert 20 according to the invention is now described.

Figure 8:
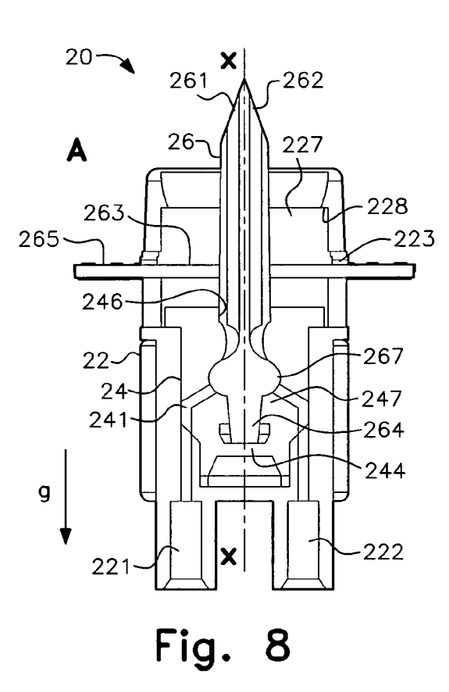
FIG. 8 shows a cross-sectional view, similar to that of FIG. 7, in which the insert according to the invention is in a first closed configuration.

FIG. 8 shows an insert 20 according to the invention where the spike 26 is in the closed position A. In this configuration, the channels 261 and 262 of the spike 26 are closed off by the walls of the seat 246 inside which the spike 26 slides. Moreover, the channels 241 and 242 of the resilient element 24 are closed off by the body of the spike 26 or, more specifically, by the bulges 267. Moreover, in the closed configuration A, the force exerted by the resilient thrusting surface 244 on the tang 264 keeps the spike 26 in contact with the upper rests 223 defined by the main body 22.

Figure 9:
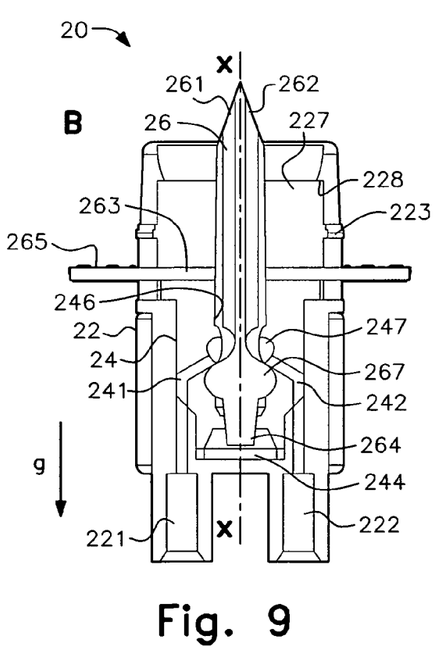
FIG. 9 shows a cross-sectional view, similar to that of FIG. 7, in which the insert according to the invention is in a second open configuration.

FIG. 9 shows an insert 20 according to the invention where the spike 26 is in the open position B. In this configuration, the channels 261 and 262 of the spike 26 are in communication with the channels 241 and 242 of the resilient element 24. Moreover, in the open configuration B, the force exerted by the resilient thrusting surface 244 on the tang 264 tends to separate the spike 26 from the bottom contact with the resilient element 24 and to bring it back into contact with the upper rests 223 defined by the main body 22.

The transition from the closed configuration A into the open configuration B is usually obtained by means of engagement of a vial 18 on the insert 20. In particular, when a user presses the stopper 182 of the vial 18 against the spike 26, the stopper 182 itself is perforated. In this way the spike 26 penetrates inside the vial 18, connecting it with the channels 261 and 262. It should be noted that, during this step, the spike 26 does not travel along the axis X, owing to the force exerted on the tang 264 by the resilient thrusting surface 244 and the friction between the seat 246 and the body of the spike 26. These forces therefore ensure that the spike 26 remains in the closed position A. In this position, the channels 261 and 262 of the spike and the channels 241 and 242 of the resilient element are closed.

When the top of the spike 26 has penetrated inside the vial 18, the stopper 182 of the vial comes into contact with the flange 263. From this point onwards a further pressure exerted by the user on the vial 18 along the direction of the axis X produces integral displacement of the vial 18 and the spike 26. During this displacement the force exerted by the user must overcome the resistance exerted by the resilient thrusting surface 244 and by the seat 246. At the end of this displacement, the head 180 of the vial 18 is positioned inside its seat 227 and the teeth 228 snap-engage so as to keep it in position. The teeth 228 therefore produce a reaction against the force exerted by the resilient surface 244. In this configuration the spike 26 is situated in the open position B. The first channel 261 of the spike 26 is connected to the first channel 241 of the resilient element 24 and to the first channel 221 of the main body; similarly, the second channel 262 of the spike 26 is connected to the second channel 242 of the resilient element 24 and to the second channel 222 of the main body. In this way, the inside of the vial 18 is connected to the exterior by means of two separate ducts.

In particular, when the insert 20 is in the open configuration with the vial 18 engaged on it, liquid is able to flow from the inside of the vial 18 towards the outside, typically towards the circuit 16 or an infusion line. At the same time, air is also able to flow from the outside towards the inside of the vial 18. In this way, the liquid volume supplied is replaced inside the vial 18 by an identical volume of air so as to maintain the pressure equilibrium.

Finally, when the vial 18 is removed from the insert 20, the spike 26 follows the vial 18 during the movement along the axis X owing to the thrusting force exerted on the tang 264 by the resilient thrusting surface 244. In this way the spike 26 is brought back automatically into the closed position A without the need for any specific action on the part of the user.

It should be noted how the insert 20, owing to its structure described above, in general is able to assume the open configuration only when a vial 18 is present and connected to it and to return into the close configuration when the vial 18 is removed. The insert 20 according to the invention is therefore adapted to avoid contamination and to enhance sterility of the circuit 16 since the spike 26 is brought back automatically into the closed position when no vial 18 is attached.

From this point of view the option of providing the lugs 265, which allow the user to adjust manually the configuration of the insert 20, must be carefully considered during the design stage.

Figure 1:
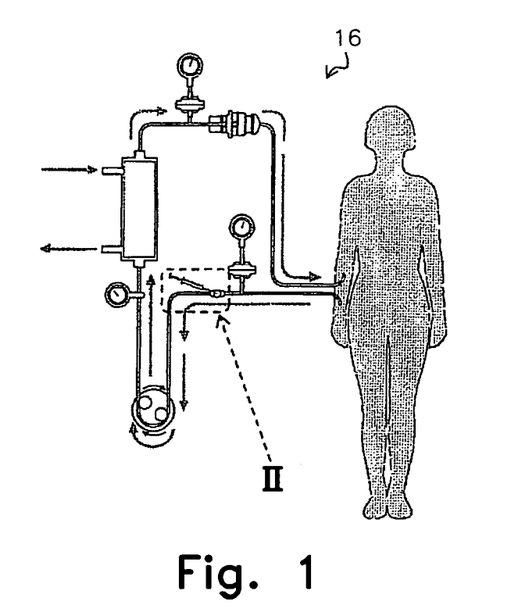
FIG. 1 shows in schematic form an extra-corporeal circuit used in therapeutic treatment.
Figure 2:
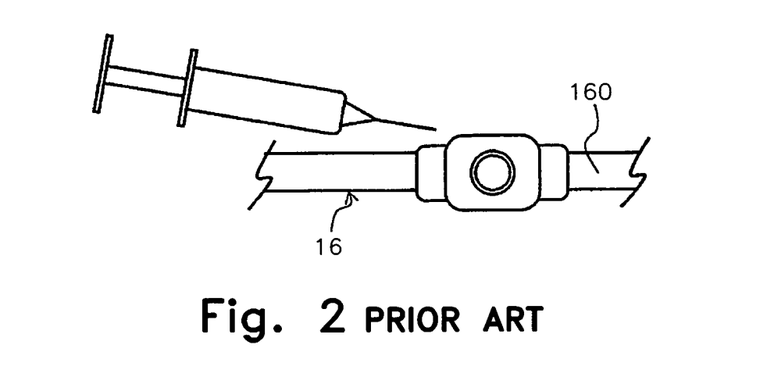
FIG. 2 shows schematically the detail, indicated by II, in FIG. 1, of the piercible cap and a syringe for administering substances according to the prior art.
Figure 3:
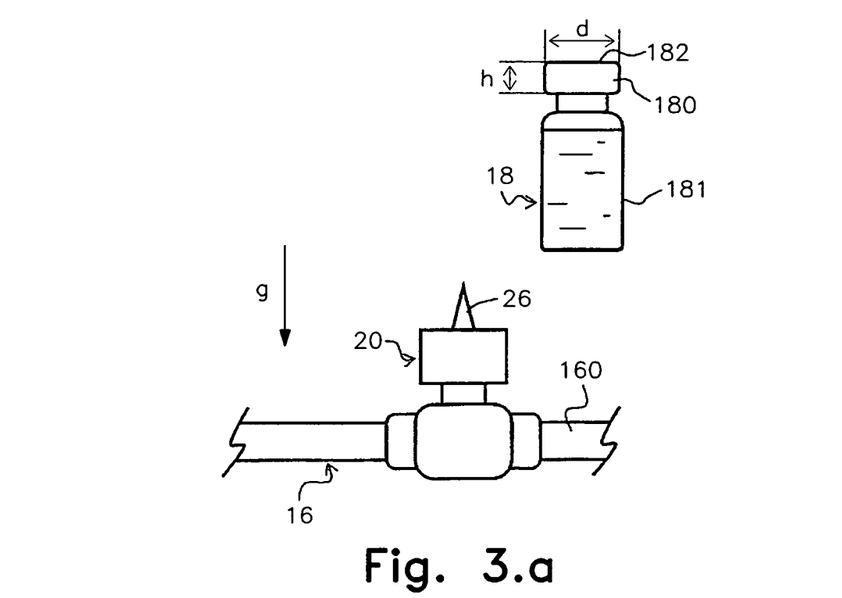
Figure 4:
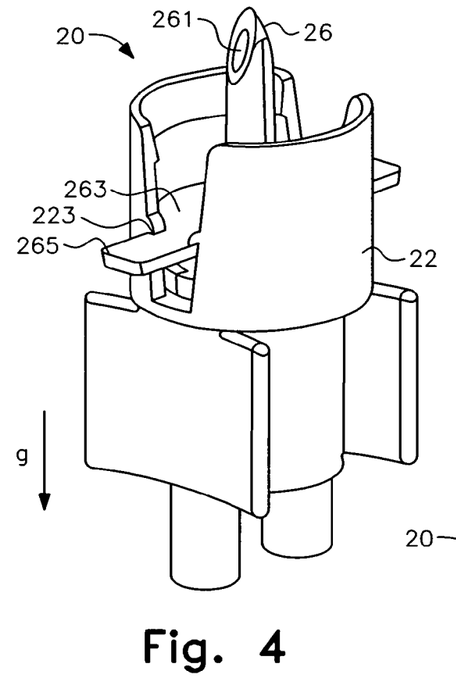
FIG. 4 shows schematically a perspective view of an insert according to the invention in a first closed configuration.
Figure 5:
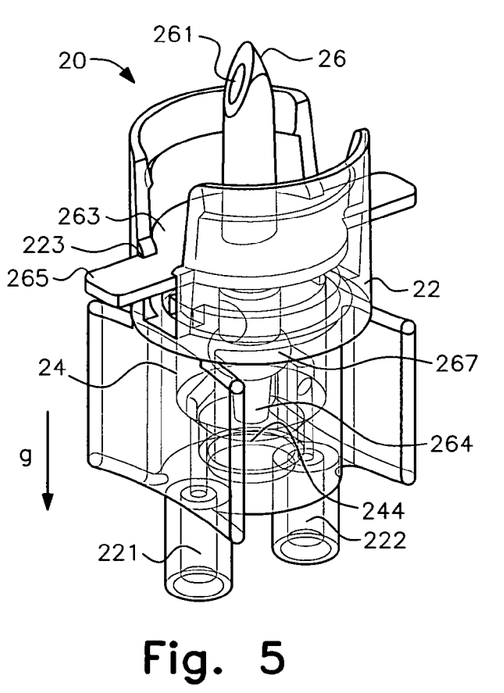
FIG. 5 shows schematically a view similar to that of FIG. 4 in which some parts of the insert are shown in semi-transparent form.
Figure 6:
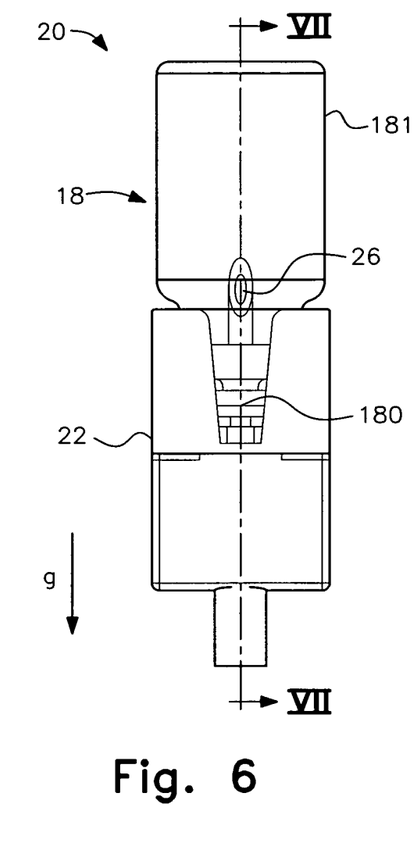
FIG. 6 shows schematically a side view of an insert according to the invention and a vial engaged thereon.
Figure 7:
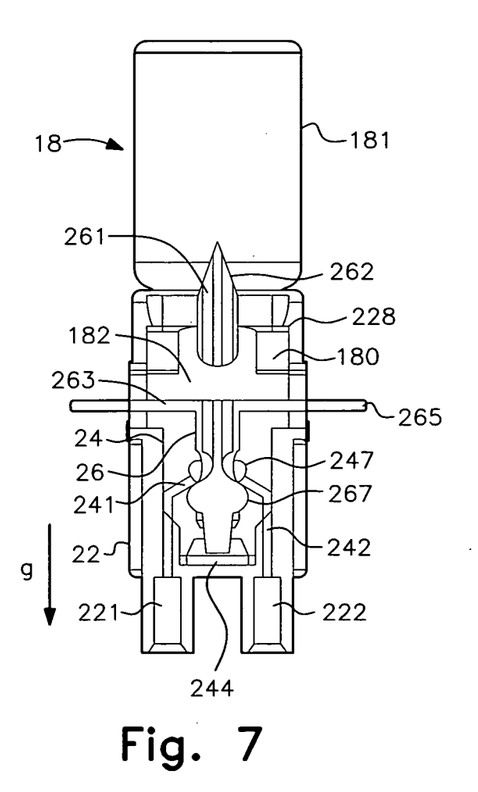
FIG. 7 shows a cross-sectional view along the line VII-VII of FIG. 6.

The insert 20 according to the invention is preferably connected to an extra-corporeal circuit 16 in correspondence with a drip chamber 161, as per the solution shown in the FIG. 3.*b*. The drip chamber is a container which allows the liquid which flows inside the extra-corporeal circuit 16 and which must be infused into the patient to drip through an air reservoir 162. This dripping action is intended to remove from the liquid any gas bubbles which could be dangerous for the patient.

According to this embodiment, the two channels 221 and 222 of the main body 22 emerge inside the drip chamber 161. In this way, once the vial 18 has been connected to the insert 20 and the spike 26 brought into the open position B, liquid flows inside one of the two channels from the vial 18 to the drip chamber 161, while inside the other channel air flows from the air reservoir 162 to the vial 18.

This operating arrangement is particularly advantageous. In fact, the same pressure present inside the circuit 16 is established inside the channels and the vial 18. Thus, supplying of the liquid is not affected by any pressure differences between the inside of the circuit and the external environment. Moreover, the air which enters inside the vial 18 from the circuit 16 is sterile and therefore does not risk contaminating at all the liquid which is still to be supplied from the vial 18. The use of a device for delivering a therapeutic substance directly from the vial 18 into the drip chamber 161 is disclosed in the European patent application 09 175 001.8, filed on Nov. 4, 2009 by the same applicant. Reference is made here to that previous application for a detailed description of the drug delivery in the drip chamber, both in terms of working principles and in terms of advantages.

According to other embodiments, the insert 20 according to the invention may be connected to the circuit 16 along any pipe 160, as shown in the solution according to FIG. 3.*a*. According to this embodiment, one of the two channels in the main body 22, for example the first channel 221, leads into the pipe 160 of the circuit 16, while the other of the two channels, for example the second channel 222, leads into the external environment. In this way, once the vial 18 has been connected to the insert 20 and the spike 26 brought into the open position B, liquid flows inside the first channel from the vial 18 to the pipe 160, while inside the second channel air flows from the external environment to the vial 18.

This operating arrangement requires a number of additional features compared to the arrangement described above. In fact, it is not possible to ensure beforehand that a pressure equilibrium is established inside the channels and the vial 18. In fact it is not possible to ensure beforehand that the pressure inside the circuit 16 is exactly the same as the atmospheric pressure present in the external environment. In other words, supplying of the liquid could be affected by any pressure differences between the inside of the circuit and the external environment. Moreover, the air which enters inside the vial 18 from the outside environment generally is not sterile and therefore may risk contaminating the liquid which is still to be supplied from the vial 18. This problem may be solved, in a known manner, by means of a semipermeable membrane which is arranged at the end of the channel connected to the external environment. The membrane allows the air alone to pass through and prevents the passage of any contaminating agents.

In accordance with one embodiment of the invention, means for regulating the liquid flow out of the vial 18 may be provided. In particular it is possible to envisage means—known per se in the sector relating to the infusion of liquids for medical use—able to vary the flow cross-section of the channel which conveys the liquid from the vial 18 into the circuit 16. Some of these means are for example described in the documents U.S. Pat. No. 4,270,725 and EP 1 731 185.

With regard to the embodiments of the insert 20 and the circuit 16 according to the invention as described above, the person skilled in the art may, in order to satisfy specific requirements, may make modifications to and/or replace parts described with equivalent parts, without thereby departing from the scope of the accompanying claims.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An insert for an infusion of drugs, said insert comprising
   a main body, a resilient element, and a piercing spike, with said insert being configured for connection to a vial,
   the piercing spike having an axis X and defining a first piercing spike channel and a second piercing spike channel and being movable relative to the main body along the axis X between: a closed position (A) and an open position (B), and
   the resilient element
   (i) pressing against the piercing spike so as to keep the piercing spike in the closed position (A) when no external forces are applied, and
   (ii) defining a seat inside which the spike is seated with a slight interference and inside which the spike is slideable, passing from at least one of the closed position (A) into the open position (B), and from the open position (B) into the closed position (A).

2. The insert according to claim 1, wherein the insert is configured for connection to an extracorporeal circuit or to an infusion line.

3. The insert according to claim 1, wherein the piercing spike extends mainly along the axis X and includes a flange which extends in a plane perpendicular to the axis X.

4. The insert according to claim 3, wherein the flange is configured to contact a stopper when the stopper has been pierced by the spike and is further pressed against the spike, such that a further pressure exerted on the vial along a direction of the axis X produces an integral displacement of the vial and of the spike towards the open position (B).

5. The insert according to claim 1, wherein the resilient element defines a resilient thrusting surface able to push the spike in an axial direction, towards the closed position (A).

6. The insert according to claim 1, wherein the resilient element defines internally a first resilient element channel and a second resilient element channel, the first resilient element channel and the second resilient element channel connecting the seat to an outside of the insert.

7. The insert according to claim 6, wherein the first resilient element channel and the second resilient element channel, defined by the resilient element are suitable to define respective extensions of the first piercing spike channel and the second piercing spike channel defined by the spike.

8. The insert according to claim 6, wherein, when the spike is in the closed position (A), the first piercing spike channel and the second piercing spike channel are closed off by walls of the seat inside which the spike slides, and the first resilient element channel and the second resilient element channel are closed off by a body of the spike.

9. The insert according to claim 6, wherein, when the spike is in the open position (B), the first piercing spike channel and the second piercing spike channel are in communication with the first resilient element channel and the second resilient element channel.

10. The insert according to claim 1, wherein the main body defines a seat for the resilient element, a seat for the spike, and a seat for a head of the vial.

11. The insert according to claim 10, wherein the seat for the head of the vial includes teeth for providing a snap-engaging connection between the main body of the insert and the head of the vial.

12. A vial comprising a head, wherein said head is configured, with respect to a size and a shape thereof, for matching the seat for the head of the vial defined by the insert according to claim 10.

13. The insert according to claim 1, wherein a force exerted on the spike by a resilient thrusting surface and friction between the seat of the resilient element and a body of the spike provide that, when a stopper of the vial is pressed against the spike, the stopper is perforated and the spike does not travel along the axis X, remaining in the closed position (A).

14. The insert according to claim wherein the main body and the resilient element have a two component injection moulding construction.

15. The insert according to claim combination with the vial, wherein teeth snap-engage a head of the vial so as to keep the head of the vial in position, and produce a reaction against a force exerted by a resilient surface on the spike.

16. The insert according to claim 15 in combination with the vial, wherein an inside of the vial is connected to an exterior of the vial via two separate ducts such that a liquid is able to flow from the inside of the vial towards the exterior of the vial, and at a same time, air is able to flow from the exterior of the vial towards the inside of the vial.

17. An extra-corporeal circuit comprising a drip chamber, wherein the insert according to claim 1 is connected to the drip chamber.

18. The extra-corporeal circuit according to claim 17, wherein the vial is connected to the insert, such that inside the first piercing spike channel a liquid flows from the to the drip chamber, while inside the second piercing spike channel air flows from the drip chamber to the vial.

* * * * *